(12) United States Patent
Sandra et al.

(10) Patent No.: US 6,815,216 B2
(45) Date of Patent: Nov. 9, 2004

(54) METHOD FOR SOLID-PHASE MICROEXTRACTION AND ANALYSIS, AND A COLLECTOR FOR THIS METHOD

(75) Inventors: Patrick Sandra, Kortrijk-Marke (BE); Erik Baltussen, Den Bosch (NL); Frank David, Bruges (BE)

(73) Assignee: Gerstel Systemtechnik GmbH & Co. KG, Mulheim (DE)

( * ) Notice: Subject to any disclaimer, the term of this patent is extended or adjusted under 35 U.S.C. 154(b) by 264 days.

(21) Appl. No.: 09/967,333

(22) Filed: Sep. 27, 2001

(65) Prior Publication Data

US 2002/0098594 A1 Jul. 25, 2002

Related U.S. Application Data

(63) Continuation-in-part of application No. 09/524,682, filed on Mar. 14, 2000, now abandoned.

(51) Int. Cl.[7] .............................. G01N 1/18; G01N 1/22; G01N 1/00; G01N 15/06; G01N 33/00
(52) U.S. Cl. .................... 436/178; 436/174; 436/175; 436/176; 436/177; 436/181; 422/50; 422/56; 422/57; 422/58; 422/68.1; 422/69; 422/70; 422/83; 73/1.01; 73/1.02; 73/23.2; 73/53.01
(58) Field of Search ............................. 422/50, 56, 57, 422/58, 68.1, 69, 70, 83; 73/1.01, 1.02, 23.2, 53.01; 436/174, 175, 176, 177, 181

(56) References Cited

U.S. PATENT DOCUMENTS

| 4,236,404 A | | 12/1980 | Ketchum et al. | |
|---|---|---|---|---|
| 4,914,966 A | * | 4/1990 | White, Jr. et al. | ........ 73/863.01 |
| 5,065,614 A | * | 11/1991 | Hartman et al. | ............ 73/23.35 |
| 5,403,489 A | * | 4/1995 | Hagen et al. | ............... 210/638 |
| 5,565,622 A | * | 10/1996 | Murphy | ..................... 73/61.55 |
| 5,588,988 A | | 12/1996 | Gerstel et al. | |

(List continued on next page.)

FOREIGN PATENT DOCUMENTS

| DE | 44 19 596 C1 | 6/1995 |
|---|---|---|
| DE | 196 19 790 A1 | 12/1996 |
| DE | 19753701 A1 | 6/1999 |
| DE | 197 51 968 A1 | 7/1999 |
| DE | 199 13 809 A1 | 10/2000 |
| EP | 0 523 092 B1 | 1/1993 |

(List continued on next page.)

OTHER PUBLICATIONS

Boyd, A.A. et al. "New solvent–free sample preparation techniques based on fiber and polymer technologies," *Environ. Sci. Technol.* 1994, pp. 569A–574A, vol. 28, No. 13.

Eisert, R. and Pawliszyn, J. "Design of automated solid–phase microextraction for trace analysis of organic compounds in aqueous samples," *J. of Chromatography* 1997, pp. 293–303, vol. 776.

(List continued on next page.)

*Primary Examiner*—Brian Sines
(74) *Attorney, Agent, or Firm*—M. Henry Heines; Townsend and Townsend and Crew, LLP (57) ABSTRACT

The invention relates to a method for solid-phase microextraction and analysis of substances in a carrier fluid, in which a collector is brought into contact with the stirred fluid containing the substances for a sufficient time and is then subjected to a solid-phase extraction directed at at least one substance adhering to the collector, and desorbed substances are transported for analysis by means of a carrier gas, in which the carrier fluid containing the substances is stirred in a receptacle of a magnetic stirrer by means of a coated magnetic stirring element as the collector, and/or the carrier fluid is made to move intimately relative to the collector by means of ultrasound, and then the stirring element is placed in a solid-phase extraction device.

46 Claims, 9 Drawing Sheets

U.S. PATENT DOCUMENTS

| | | | |
|---|---|---|---|
| 5,664,938 A | | 9/1997 | Yang |
| 5,693,228 A | * | 12/1997 | Koehler et al. ............. 210/656 |
| 2002/0098594 A1 | | 7/2002 | Sandra et al. |

FOREIGN PATENT DOCUMENTS

| | | |
|---|---|---|
| WO | WO 91/15745 A1 | 10/1991 |
| WO | WO 97/11763 A1 | 4/1997 |
| WO | WO 98/41855 A1 | 9/1998 |

OTHER PUBLICATIONS

Geppert, H. "Solid–phase microextraction with rotation of the microfiber," *Anal. Chem.* 1998, pp. 3981–3982, vol. 70.

Grote, C. et al. "An automatic analyzer for organic compounds in water based on solid–phase microextraction coupled to gas chromatography," *Anal. Chem.* 1999, pp. 4513–4518, vol. 71.

* cited by examiner

METHOD FOR SOLID-PHASE MICROEXTRACTION AND ANALYSIS, AND A COLLECTOR FOR THIS METHOD

CROSS REFERENCE TO RELATED APPLICATION

This application is a continuation-in-part of application Ser. No. 09/524,682, filed Mar. 14, 2000 now abandoned, the contents of which are incorporated herein in their entirety.

BACKGROUND OF THE INVENTION

1. Field of the Invention

The invention relates to a method for solid-phase microextraction and analysis of substances originating for example from a carrier fluid and to a collector for use within this method. The invention also relates to a collector, which serves as a passive collector in a gaseous, for example loaded environment containing substances to be analyzed and a method for solid-phase microextraction and analysis of these substances.

2. Description of the Related Art

A method of this type is known from Boyd-Boland et al., Environ. Sci. Technol. Vol. 28, No. 13, 1994, 569A–574A and from EP 0,523,092 B1, in which a special syringe is used, which has a fiber which can be telescoped through the syringe needle. The fiber, which is expediently coated, is brought into contact with the carrier fluid which contains the substances to be examined and at the same time is being stirred, after which the fiber is retracted and the syringe needle is introduced into a feeding device of an analyzer, followed by desorption of adhering substances using a carrier gas. The fiber has only a very limited absorption capacity for substances which are to be examined and, moreover, is only dipped into the stirred carrier fluid, so that consequently the sensitivity of the analysis itself leaves something to be desired if the coated fiber is vibrated. In addition, it is known from DE 196 19 790 C2 to have the microfiber functioning as a collector rotate about its own axis by means of an electric motor with a rotational speed of one's choice.

SUMMARY OF THE INVENTION

An object of the invention is to provide a method for solid-phase microextraction and analysis of substances to be analyzed and originating for example from a carrier fluid, which provides a significantly improved sensitivity.

Another object of the invention is to provide a collector for solid-phase microextraction and analysis of substances to be analyzed and originating for example from a carrier fluid.

A further object of invention is to provide a collector which may be used within the method for solid-phase microextraction and analysis of substances.

A still other object of the invention is to provide a collector as a passive collector for solid-phase microextraction and analysis of substances for example pollutants to be analyzed and originating for example from an environment.

A still other object of the invention is to provide a method for solid-phase microextraction and analysis of substances to be analyzed and originate from an environment, for example pollutants.

A subject of the invention is a method for solid-phase microextraction and analysis of substances in a carrier liquid, in which a collector is brought into contact with the stirred liquid containing the substances for a sufficient time and is then subjected to a solid-phase extraction directed at at least one substance adhering to the collector, and desorbed substances are transported for analysis by means of a carrier gas, wherein the carrier liquid containing the substances is stirred in a receptacle of a magnetic stirrer by means of a coated magnetic stirring element as collector, and/or the carrier liquid is made to move intimately relative to the collector by means of ultrasound, and afterwards the stirring element is arranged in a solid-phase extraction device.

Another subject of the invention is a collector for the solid-phase microextraction and analysis of substances to be examined, in particular for use in a thermal desorption apparatus of a gas chromatograph, comprising a carrier made from magnetic material, which is suitable as a stirring element for a magnetic stirrer and is provided with a sorbent and/or adsorbent coating for the substances to be examined.

A still other subject of the invention is a coated magnetic collector, which serves as a passive collector in a gaseous, for example loaded, environment containing substances to be analyzed.

A still other subject of the invention is a method for the solid-phase microextraction and analysis of substances in an environment, in which a collector is exposed to the environment for a sufficient time as a passive collector and then the collector is positioned in a solid-phase extraction device, desorbed substances being transported for analysis by means of a carrier gas.

The use of a stirring element which is actuated by a magnetic stirrer and/or an ultrasonic agitator increases the accuracy of analysis very considerably, and moreover it is possible to use large-volume receptacles, for example liter receptacles, for the fluid containing the substances to be examined.

Further objects, advantages and embodiments of the invention are evident from the following description.

The invention is explained in more detail below with reference to exemplary embodiments of the invention, which are illustrated in the attached drawings, of a device for carrying out the method and of passive collectors.

DETAILED DESCRIPTION OF THE INVENTION AND PREFERRED EMBODIMENTS

Figures 1, 2, 3, 4:
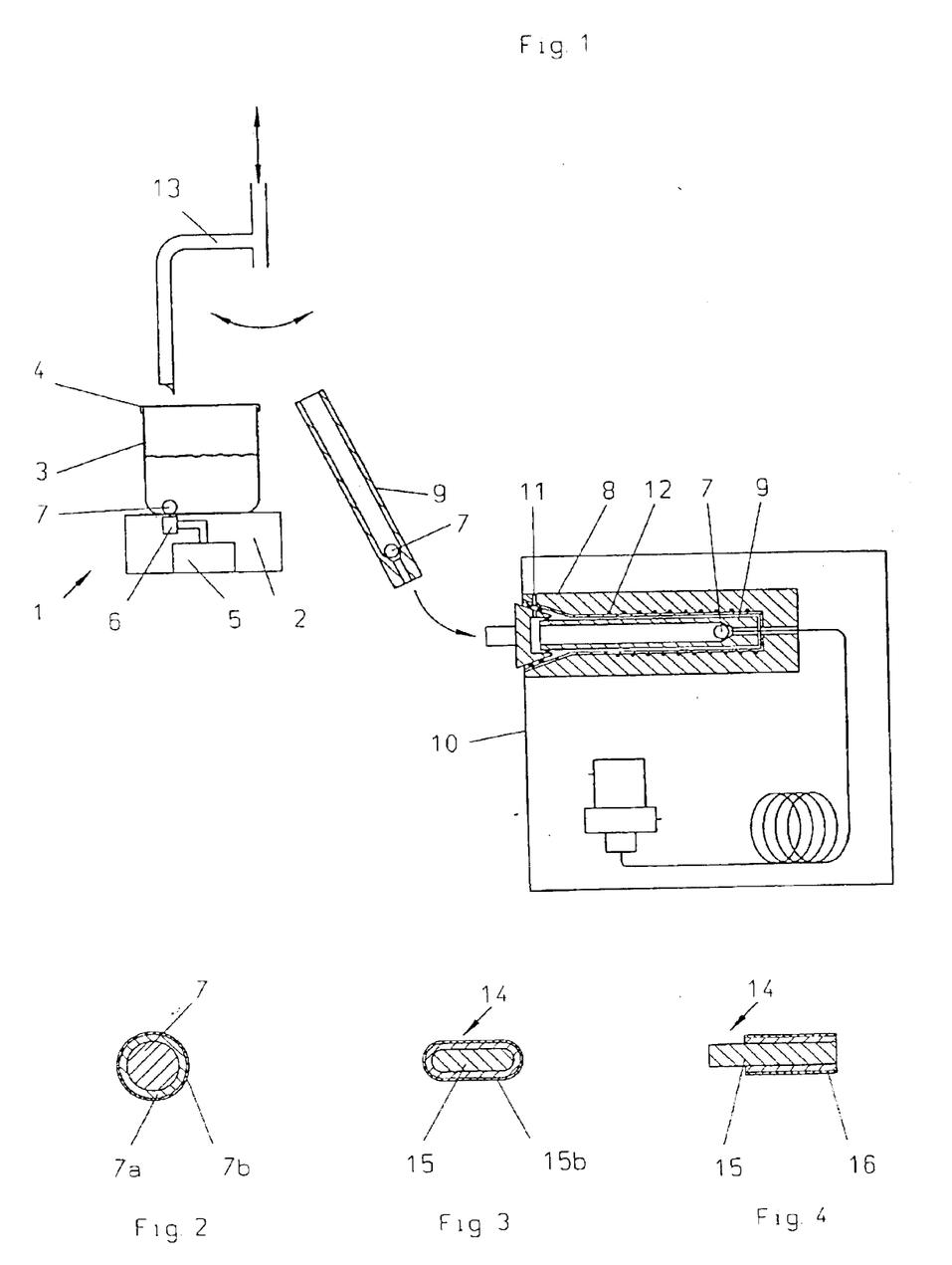
FIG. 1 is a diagrammatic view of a device for carrying out the method for solid-phase microextraction and analysis of substances which are in a carrier fluid.
FIGS. 2 to 4 show various embodiments of passive collectors, in section.

In accordance with FIG. 1, a magnetic stirrer 1 is provided, which comprises a receptacle 3 which is positioned on a base 2 and is in the form of a beaker and may expediently be closed at its top side by a septum 4. Before it is closed by the septum 4, the receptacle 3 receives a carrier fluid containing substances which are to be analyzed. The receptacle 3 may have been filled and closed in advance at a sampling point. The carrier fluid may be water and/or an organic solvent or a mixture thereof or liquefied gas.

The base 2 comprises an electric motor 5, the shaft of which bears a magnet 6 eccentrically. In the receptacle 3, there is a stirring ball 7 made from ferromagnetic material, such as iron or steel, which is advantageously glass- or plastic-sheathed and has a diameter in the range of a few millimeters. The plastic sheathing 7a used may, for example, be polytetrafluoroethylene or another fluorinated hydrocarbon polymer. The stirring ball 7 is preferably covered with an active phase 7b for sorption/adsorption of substances contained in the carrier fluid. This may be a coating selected from the group comprising polyethylene glycol, silicone, polyimide, octadecyltrichlorosilane, polymethylvinylchlorosilane, liquid-crystal polyacrylates, grafted self-organized monomolecular layers and inorganic coating materials.

The stirring ball 7 can be stirred for a sufficient time during which it comes into intensive contact with the carrier fluid and therefore with the substances contained therein and sorbs and/or adsorbs the latter, so that it serves as a collector. After the end of stirring, the stirring ball 7 is picked up and introduced in a solid-phase extraction device, preferably a desorption device 8. The latter advantageously comprises a desorption tube 9 with a diameter section whose diameter is slightly greater than that of the stirring ball 7, followed, via a frustoconical section, by a diameter section whose diameter is smaller than that of the stirring ball 7. The desorption device 8 is part of an analyzer 10, for example of a gas chromatograph, connected to a carrier gas port 11, so that carrier gas flows through the desorption tube 9 passing the stirring ball 7, desorbing substances adhering thereto, and can supply these substances for analysis. The desorption device 8 preferably comprises a heating device 12, in order to carry out a thermal desorption.

The stirring ball 7 can be removed from the receptacle 3 automatically by means of a discharging device 13 which penetrates the septum 4 and may be designed in the form of a gripping device, suction device or also as a magnet, and can be positioned in the desorption tube 9, which can then be placed automatically in the desorption device 8, so that the entire solid-phase microextraction and analysis can be performed automatically. For this purpose, an appropriate receptacle 3 for a plurality of samples can be arranged on a turntable which can rotate in steps and beneath which, in one position, the base 2 of the magnetic stirrer 1 is arranged.

In order to achieve reproducible measurements, stirring times of approximately 45 to 60 minutes are generally required.

As an alternative to a stirring element in the form of a stirring ball, it is also possible to use an element in the form of a stirring rod 14. This may have a coated rod-like carrier 15 made from ferromagnetic or paramagnetic material; in the latter case, it should have a minimum length of approximately 2 cm, while shorter lengths are also possible if ferromagnetic material is used. For example, it may be a rod-like carrier 15 which is rounded at the ends and is entirely coated with the active phase 15b (FIG. 3) or also a carrier comprising a section of wire which is surrounded by a cylindrical sheath 16 made from material of the active phase which is in the form of a flexible tube (FIG. 4). By way of example, the rod-like carrier 15 may have a diameter of approximately 3 to 6 mm.

Figure 6:
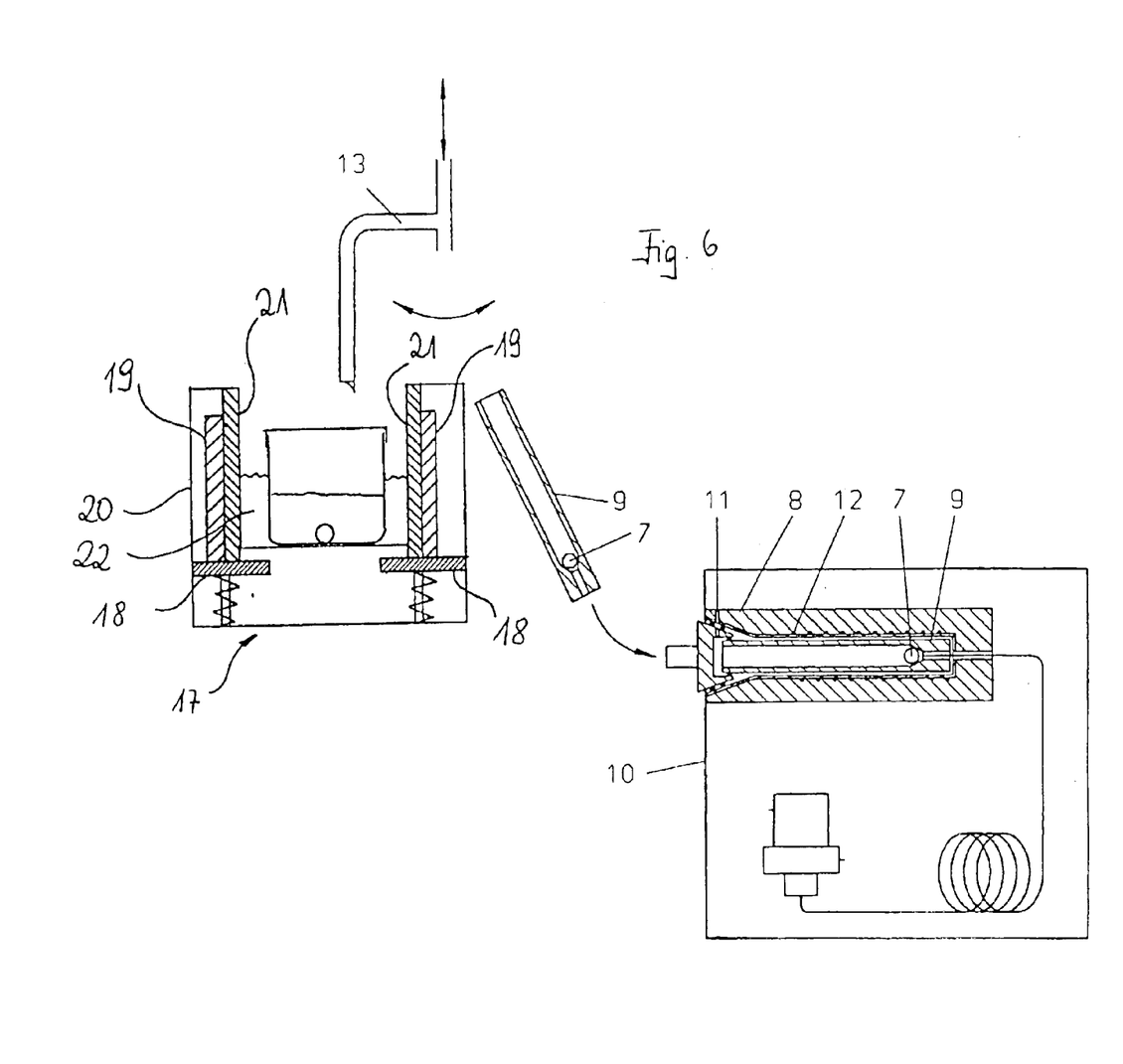
FIG. 6 is a diagrammatic view of a further device for carrying out the method for solid-phase microextraction and analysis of substances which are in a carrier fluid.

It is also possible to achieve improved analysis if the carrier fluid which contains the substances and is situated in a receptacle containing a collector, which is preferably a stirring ball 7, is alternatively or additionally set in motion by means of ultrasound. FIG. 6 shows one embodiment of such an ultrasonic stirring device as a resonator unit 17 in which one or more ultrasonic generators (vibrators) 19, which are shielded by means of insulating plate 18, are incorporated at the bottom and/or on the sides of a housing 20. A metal wall 21 which is mounted in front of the ultrasonic generator 19 and has a wall thickness of $d=n*\lambda/2$ ($\lambda$=acoustic wavelength) transmits the vibrations to a coupling liquid 22 in the resonator unit 17, preferably water, which is set in motion. The receptacle containing the substances to be analyzed is introduced into the resonator unit 17.

In this case, the receptacle 3 is also advantageously one of a magnetic stirrer, in which case stirring is carried out by means of the coated magnetic stirring ball 7 as collector, so that the ultrasound is applied in addition to the magnetic stirring.

In general, thermal, liquid or desorption by means of supercritical gases is possible.

Figure 7:
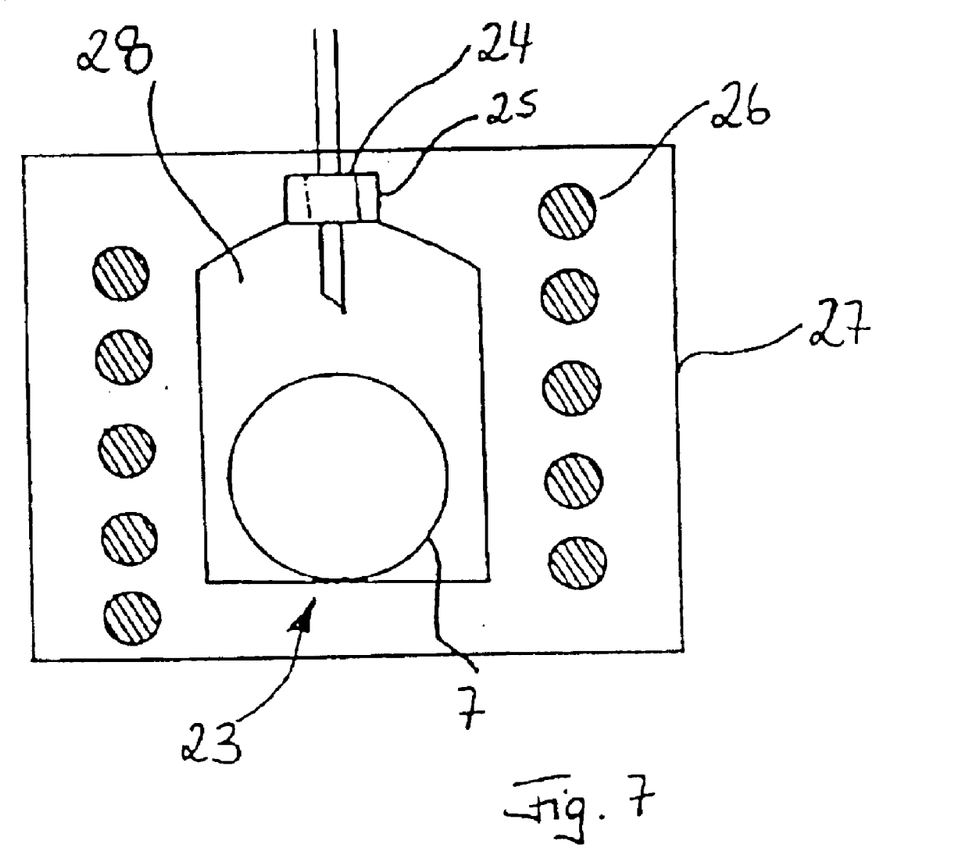
FIG. 7 is a diagrammatic view of a headspace receptacle.

As an alternative to being introduced into a thermal desorption device 8, the stirring element can be arranged in a headspace receptacle 23 (FIG. 7), the diameter of which is only slightly greater than the diameter of the stirring ball 7, by means of the discharging device 13. The headspace receptacle 23 is then closed by means of a septum 24 and a sealing ring 25, using a closure instrument, and is introduced into a headspace head 26. In the latter, the headspace receptacle 23 is preheated by means of a heating device 27 and there is a build-up of pressure, during which an equilibrium for the volatile substances to be examined with the gas phase 28 above the stirring ball 7 is established. These substances can be removed by means of a syringe which penetrates the septum 24 and can be fed to the separation column of, for example, a gas chromatograph.

As an alternative to being desorbed in a thermal desorption device 8, the stirring element may also be introduced into an extraction device containing an organic liquid, the organic liquid used exhibiting a high level of interaction with the substances to be examined and absorbing the latter—if necessary during a stirring movement of the stirring element with respect to this liquid, after which the liquid which is enriched with the substances to be examined is taken up by means of a syringe and taken to a feeding device of, for example, a gas chromatograph, in order to be fed for analysis, for example using a gas-chromatography separation column, by means of a carrier gas.

Figure 5:
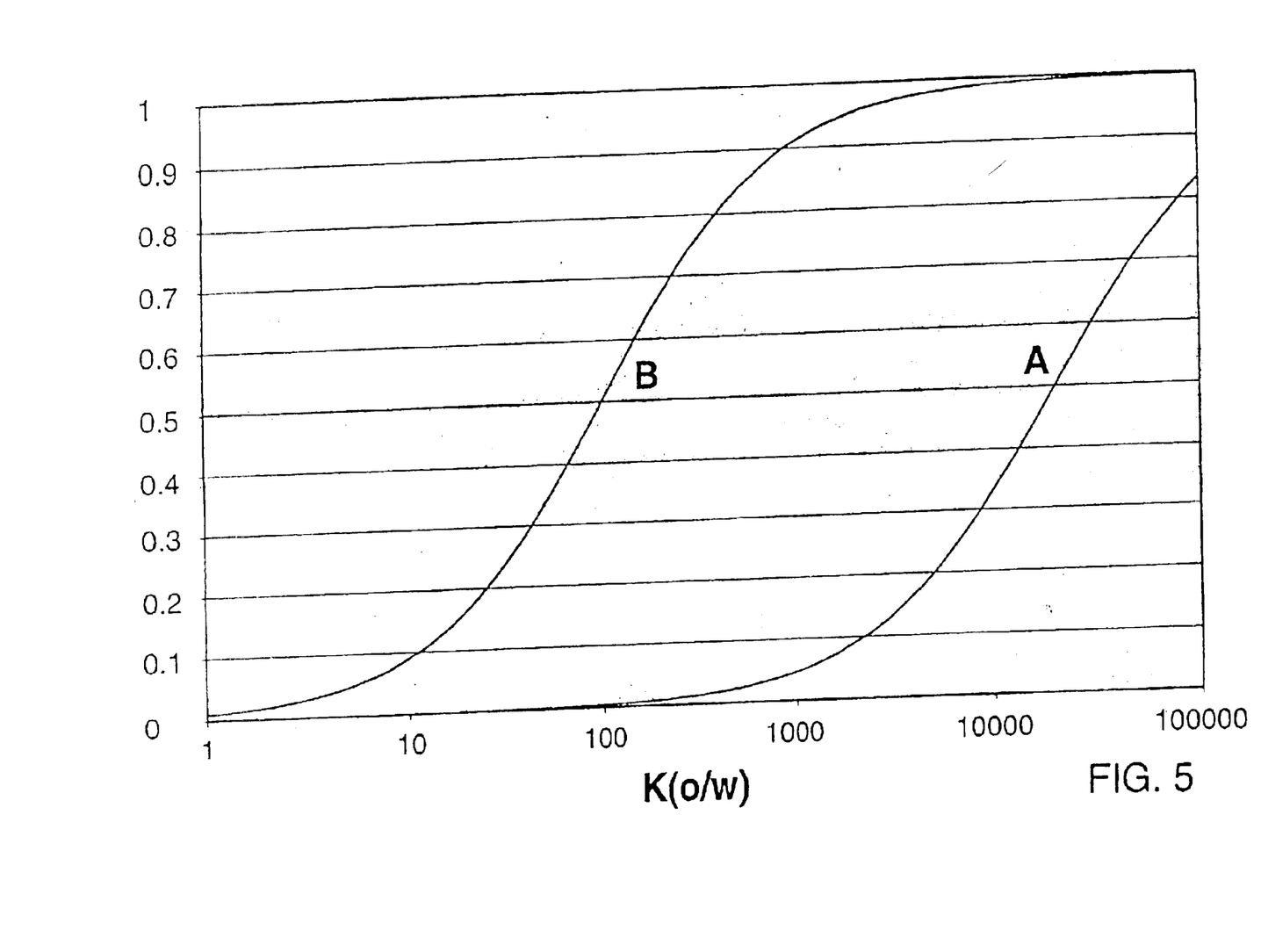
FIG. 5 shows a comparison of two equilibrium curves relating to the prior art and the invention.

Due to the use of a stirring element in a magnetic stirrer or, alternatively or additionally, in an ultrasonic agitator and its intensive contact with the carrier fluid containing the substances to be examined, it is possible to achieve a sensitivity of analysis which is orders of magnitude, for example about 1000 times, better than the use of the known fiber. FIG. 5 shows a diagram comparing the yield (plotted on the ordinate) of absorbed substances for a known fiber coated with active phase (curve A) and a stirring rod which is sheathed by active phase and has been stirred by means of the magnetic stirrer according to the invention (curve B) at mass equilibrium, the concentration quotient (K(o/w)) of a substance in octanol and water being plotted on the abscissa. This coefficient (for normal temperature) can be found in the literature for a wide range of substances. For example, if this concentration quotient is 100, it can be seen from the diagram shown in FIG. 5 that in this case the coated fiber provides a yield of approximately 1% and the invention provides a yield of approximately 50%. At a concentration quotient of below 100, the coated fiber cannot generally carry out any reliable measurement, while the sheathed stirring element generally still allows absolute reliable measurements. Generally, the covered stirring element improves the measurement accuracy considerably, i.e. by powers of 10, and widens the measurement range considerably, in that the sensitivity of analysis is improved approximately by a factor of 1000. With the sheathed stirring element, there is generally no need for the sensitivity of analysis to be improved by heating the liquid containing the substances to be examined, as is necessary in many cases for a coated fiber and also causes measurement errors.

Moreover, a stirring element of this type may be arranged as a passive collector in a gaseous, for example loaded, environment containing substances to be examined or may be carried by a person working in the environment, in which case the passive collector is exposed to the environment for a sufficient time and afterwards the substances which it has sorbed and/or adsorbed are subjected to extraction, after which desorbed substances are transported for analysis by means of a carrier gas via a feeding device, for example in order to monitor personal exposure to pollutants.

Figure 8:
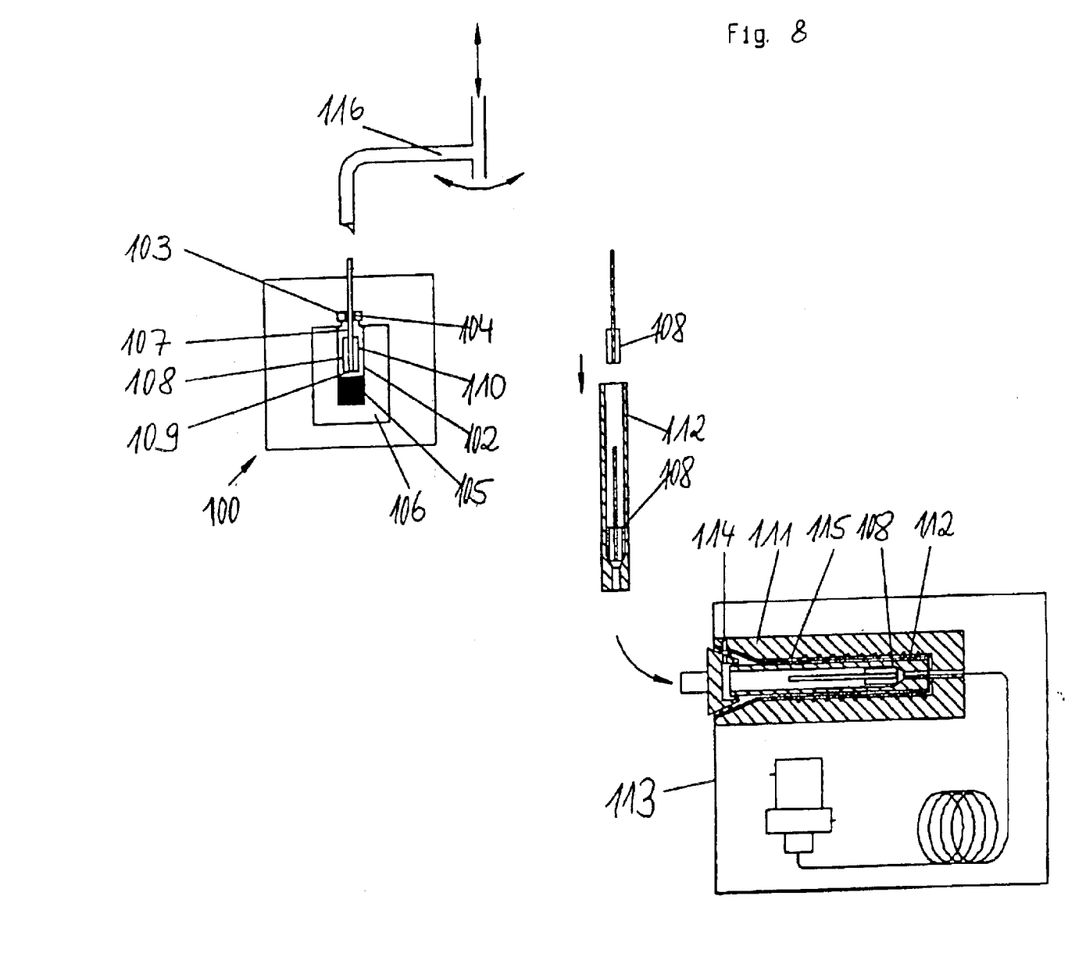
FIG. 8 diagrammatically depicts a device for carrying out the method for solid-phase microextraction and analysis of substances which are in a carrier liquid.

In the heatable headspace extraction apparatus 100 illustrated in FIG. 8, there is a headspace vessel 102, which is expediently closed off at the top by a headspace vessel cap 103 and by means of a septum 104, the headspace vessel 102, before it is closed off, receiving a carrier liquid 105 containing substances which are to be investigated and may be in apolar form, of medium polarity or, if appropriate, may even be polar. The carrier liquid may be water and/or an inorganic solvent or solvent mixture or liquefied gas.

The headspace extraction apparatus 100 includes a heating apparatus 106, which can be used to heat the contents of the headspace vessel 102. An equilibrium of the volatile compounds is established between the carrier liquid 105 and a gas phase 107 above it. When heated, additional pressure is built up inside the headspace vessel 102. In the gas phase 107 above the carrier liquid 105 there is a collector 108 which comprises an inert support 109, for example a rod-like glass tube (closed off from the outside at least during the headspace extraction), and a hose 110 which has been pushed on, at least partially surrounds the glass tube and comprises hydrophobic material as active phase. The hose 110 is used for the sorption of substances which are situated in the gas phase 107, are derived from the carrier liquid 105 and are to be investigated, the analysis of which can then be carried out substantially without water. The material of the hose 110 comprises, as active sorption phase, by way of example substances selected from the group consisting of polydimethylsiloxane, polyethylene glycol, silicone, polyimide, polymethylvinylchlorosilane, octadecyltrichlorosilane, liquid-crystal polyacrylates, grafted self-organized monomolecular layers and inorganic coating materials, or consists of these materials.

The collector 108 is exposed to the gas phase 107, above the carrier liquid 105, for a sufficient time, and therefore exposed to the substances which are to be investigated, of which there is then an increased level in the hose 110 of the collector 108, which has a sorptive action on the substances. On account of the considerable thickness of the hose 110, the substances which are to be investigated can accumulate in the hose 110 until virtually complete saturation, since the equilibrium of the generally volatile substances which is established between the carrier liquid 105 and the gas phase 107 can be shifted towards the gas phase on account of permanent sorption of these substances in the active phase of the collector 108.

After the sorption or a predetermined time has ended, the collector 108 is picked up and is placed in a solid-phase microextraction apparatus, preferably a desorption apparatus 111. The latter expediently comprises a small desorption tube 112 with a diameter section whose diameter is slightly greater than that of the collector 108 and which is adjoined, via a frustoconical section, by a diameter section whose diameter is less than that of the collector 108. The desorption apparatus 111 is connected, as part of an analysis unit 113, for example a gas chromatograph, to a carrier gas connection 114, so that carrier gas can flow through the desorption tube 112 past the collector 108, so that substances adhering thereto are desorbed and can pass these substances for analysis. The desorption apparatus 111 preferably comprises a heating device 115, in order to be able to carry out thermal desorption.

The entire method for carrying out the solid-phase microextraction and analysis of substances in a carrier liquid can be fully automated, by the collector 108 being automatically removed from the headspace vessel 102 with the headspace vessel cap 103 and the septum 104 by means of a transfer member 116, which may be designed in the form of a gripper, sucker or as a magnet, and transferred into the desorption tube 112. The desorption tube 112 is then likewise automatically placed in the desorption apparatus 111, so that the entire solid-phase microextraction and analysis can be performed automatically.

For this purpose, for a plurality of samples corresponding headspace vessels 102 may be arranged on a turntable which can be rotated in steps and next to which, in one position, the headspace extraction apparatus 100 and in a further position the transfer member 116 are arranged.

To enable reproducible measurements to be carried out, sorption times of a few minutes up to 60 min are generally required, depending on the volatility of the substances to be investigated and therefore any heating operations which may additionally be required.

Figure 9:
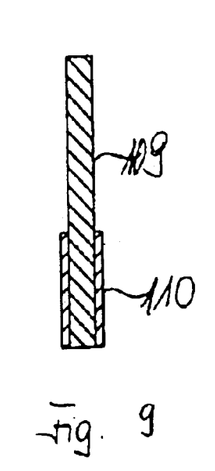
FIGS. 9 to 11 show various embodiments of collectors for solid-phase microextraction and analysis of substances which are in a carrier liquid, in section.

In the embodiment of the collector 108 illustrated in FIG. 9, the inert support 109 is in the form of a rod and is at least partially surrounded by the hose 110 which has a sorptive action.

Figure 10:
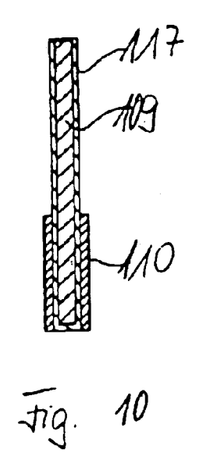

However, the collector 108 may also be provided with a ferromagnetic or paramagnetic support 109 which is surrounded by an inert casing of, for example, glass, in which case the hose 110 at least partially surrounds the inert casing 117, as illustrated in the embodiment shown in FIG. 10. The collector 108 may then be detachably secured to a separate magnetic or magnetizable holder (not shown). However, any other type of detachable holder using a plug connection, a screwed connection, or any other suitable connection for detachably securing it to the collector 108 is possible, for example if a magnetic support 109 is not used.

The inert support 109 preferably has a minimum internal diameter of 0.8 mm, in particular has an internal diameter of 1.0 to 1.3 mm, since this minimum internal diameter is expedient in order to provide sufficient hose material for sorption.

In the embodiments of the collector 108 with a ferromagnetic or paramagnetic support 109, it is preferable to use a transfer member 116 with a magnetic action.

Figure 11:
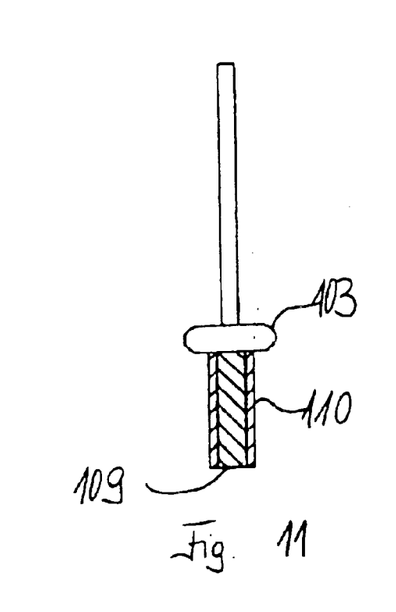

In the further embodiment illustrated in FIG. 11, the collector 108 is formed integrally with the headspace vessel cap 103. This unit can be fitted onto the desorption tube 112, so as to close off the latter in a sealed manner, by means of the transfer member 116. The hose 110 virtually completely surrounds the inert support 109.

Depending on the nature of the substances to be investigated, the hose 110 should have a length of preferably 5 to 60 mm, in order to provide sufficient sorption material.

EXAMPLE AND COMPARATIVE EXAMPLE

The following examples demonstrate the advantages of the present HSSE method over the known SPME method.

An analysis using the HSSE method was carried out under the following conditions: 40 ppb of a solvent mixture (C6–C13) were added to 10 mL of an aqueous sample and the mixture was introduced into a 250 mL Erlenmeyer flask, which was closed off by means of a septum coated with aluminum foil, so that a gas phase formed above the liquid. A glass rod which was encased by 50 mg of polydimethylsiloxane (PDMS) as pushed-on hose 110, was held in the gas phase as inert support 109; the hose 110 surrounded the inert support 109 over a length of 5 cm and with a wall thickness of 0.2 mm. The enclosed glass rod was introduced into a thermal desorption apparatus by means of a small thermal desorption tube and was subjected to thermal desorption, during which the thermal desorption tube, which had been heated to 40° C., was heated in splitless mode to 250° C. with a heating rate of 60° C./min, and the desorbed substances to be investigated were then transferred to a cold charging system by means of carrier gas and via a transfer line. In the cold charging system, in this case a Tenax-filled quartz liner, the substances to be investigated were received at −150° C. and then released again using a heating rate of 600° C./min up to a final temperature of 250° C. with a split ratio of 1:50, in order to obtain signal peaks which are suitable for the quantity of sorbed substances. The Tenax-filled quartz liner in the cold charging system prevents the highly volatile components from breaking through. The substances to be investigated were then transferred to a GC column by means of a carrier gas; in this example, a GC column which was 30 m long, had an internal diameter of 250 $\mu$m and a film thickness of 1$\mu$m was used. The GC column was heated by a furnace which surrounds it and initially held the temperature at 30° C. for 1 min and then raised it to 300° C. with a heating rate of 10° C./min. The substances to be investigated were analyzed using an MSD 5973 (mass-selective detector) in scan mode in the range from 20–400 amu (atomic mass units).

In the comparative example using the known SPME method, the specimen was prepared in a similar manner and a fiber coated with PDMS in a layer thickness of 100 $\mu$m was held in the gas phase in the closed Erlenmeyer flask. This layer thickness approximately corresponds to a coating quantity of 0.5 mg of PDMS. The thermal desorption and cold charging likewise took place in a similar manner to the HSSE method, but the phase of heating up the cold charge and the subsequent transfer to the GC column was only able to take place in splitless mode, on account of the small quantities of substance present, while the subsequent analysis was once again carried out in a similar manner to the HSSE method.

Figure 12:
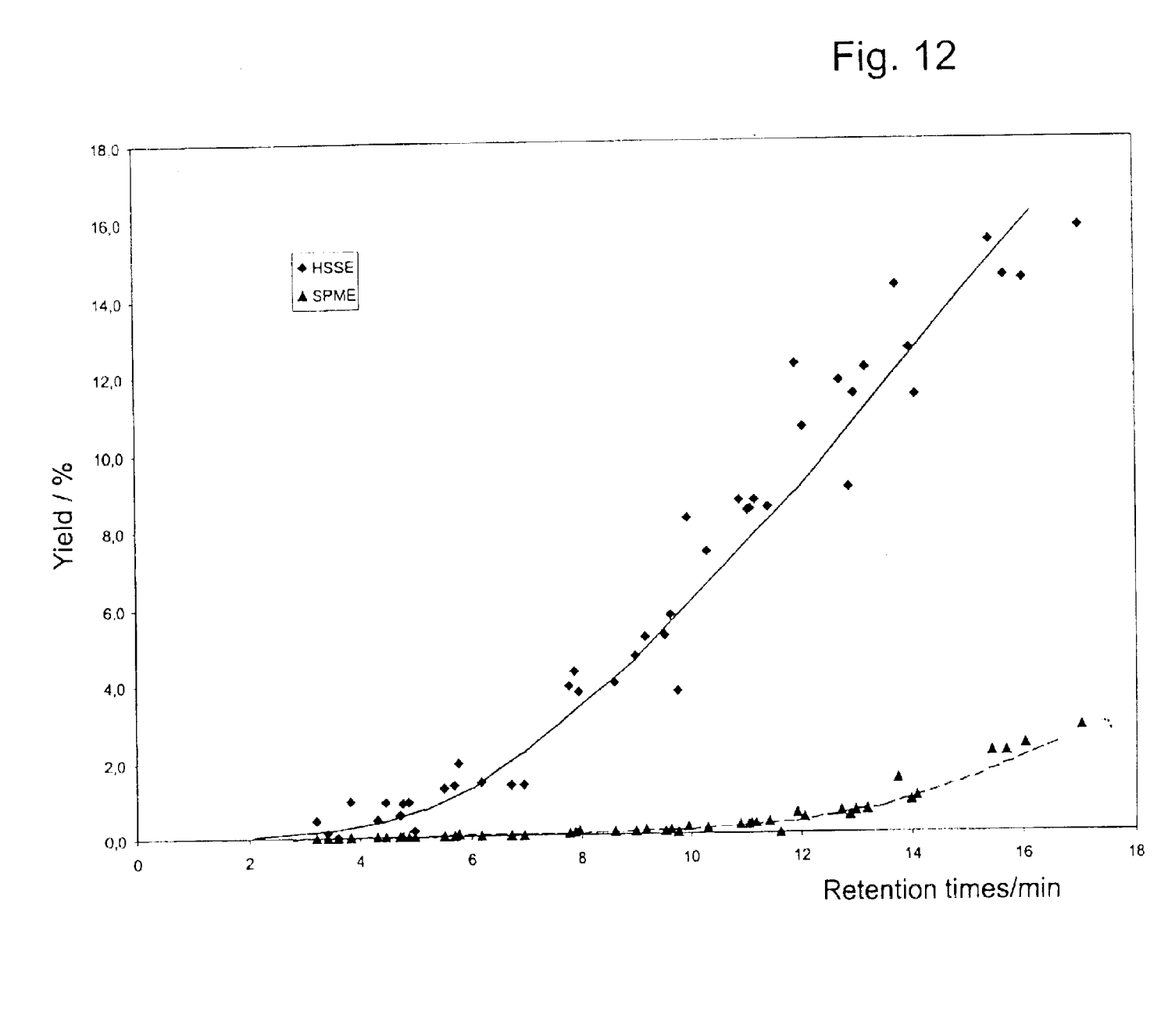
FIG. 12 shows a comparison of the yield with regard to a method belonging to the prior art (SPME method) and the present method (headspace sorptive extraction method: HSSE method).

FIG. 12 shows a comparative diagram illustrating the yield (plotted on the ordinate) for the hose using the HSSE method of the example and for the coated fiber of the SPME method of the comparative example; the retention time of the substances investigated is plotted on the abscissa. If the retention time is approximately 10 min, it can be seen from the diagram shown in FIG. 12 that, in this case, the coated fiber of the SPME method gives a yield of virtually 0%, while the HSSE method gives a yield of approximately 6%. With retention times of less than 10 min, the coated fiber of the SPME method generally does not allow a reliable measurement to be carried out (cf. also FIG. 14), while the hose generally allows reliable measurements (cf. also FIG. 13). Overall, the comparative diagram of FIG. 12 demonstrates that, with the hose of the HSSE method, the yield is improved considerably, i.e. by at least one power of 10, and the measurement range is widened considerably, since the analysis sensitivity is improved by approximately a factor of 50.

Figure 13:
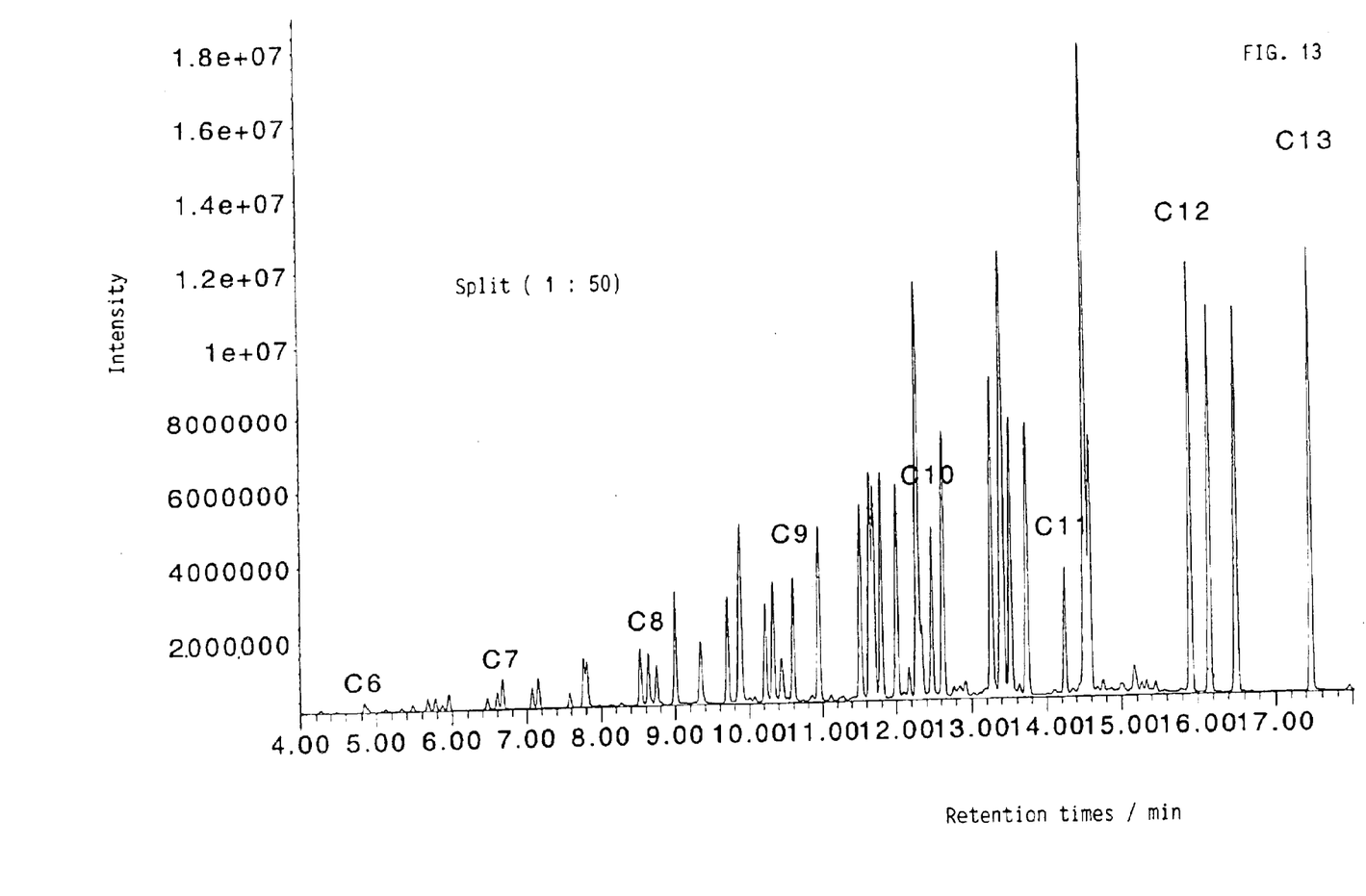
FIG. 13 shows a GC spectrum of substances which are in a carrier liquid using the present method.

FIG. 13 shows a GC spectrum using the HSSE method, in which the intensities are plotted against the retention times; this spectrum is obtained by means of the example described above and constitutes the basis for the comparative diagram shown in FIG. 12.

Figure 14:
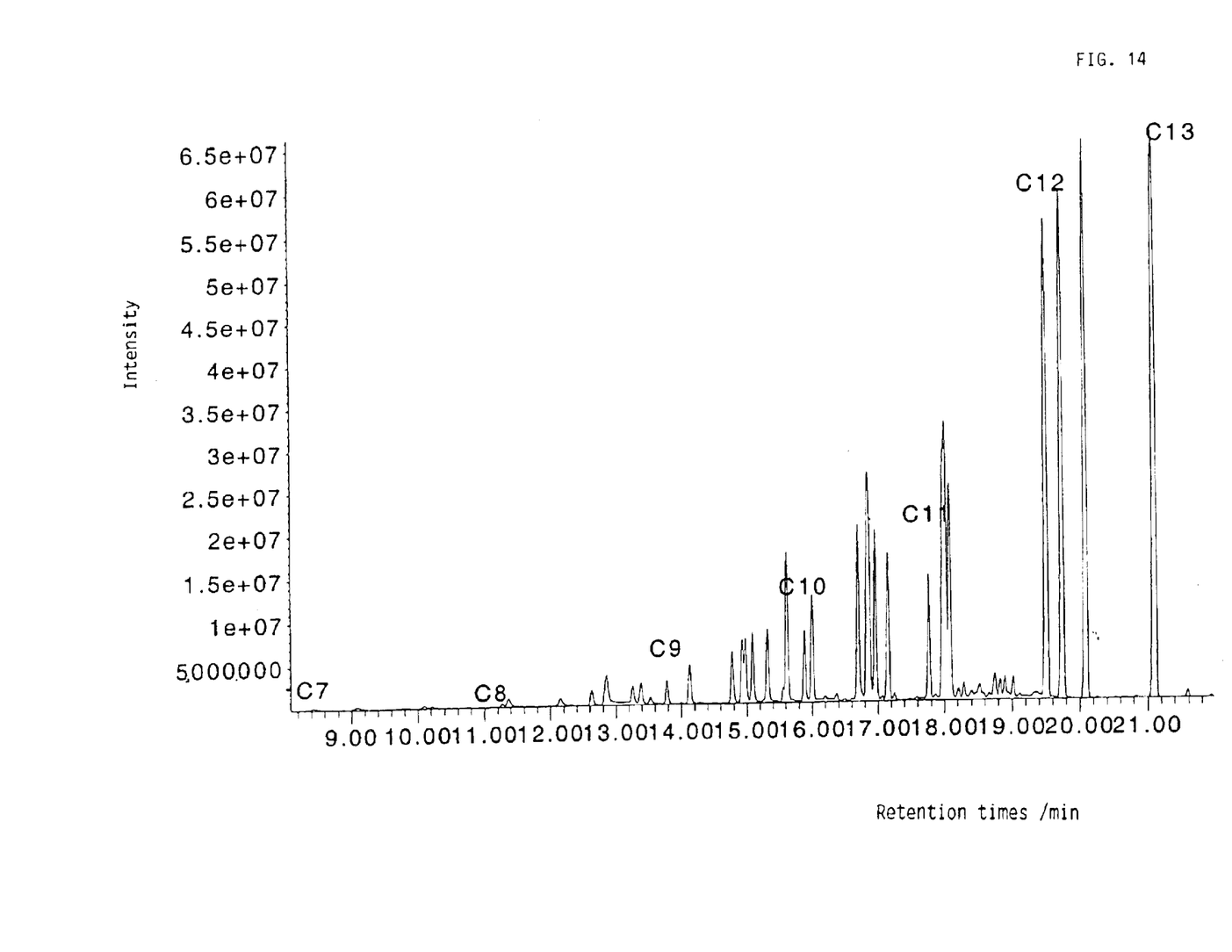
FIG. 14 shows a gas chromatography spectrum (GC spectrum) for substances which are in a carrier liquid using the SPME method.

FIG. 14 shows a GC spectrum using the SPME method, in which the intensities are plotted against the retention times; this spectrum is obtained by means of the comparative example described above and constitutes the basis for the comparative diagram shown in FIG. 12.

A comparison of FIG. 13 and FIG. 14 shows that overall the HSSE method reveals a significantly improved sensitivity and lower retention times with, at the same time, a considerably higher intensity, which in this example, moreover, emerges particularly clearly for substances with low molecular masses as well.

Although the foregoing has been a description of preferred embodiments of the invention, it will be apparent to those skilled in the art that numerous variations and modifications may be made in the invention without departing from the scope as described herein.

What is claimed is:

1. Method for solid-phase microextraction and analysis of substances in a carrier fluid, said method comprising:
   (a) charging a receptacle containing a coated magnetic stirring element with said carrier fluid,
   (b) stirring the carrier fluid for a sufficient time to cause said coated magnetic stirring element to sorb said substances from said carrier fluid,
   (c) performing solid-phase microextraction on said coated magnetic stirring element to desorb said substances therefrom,
   (d) transporting said desorbed substances to analyzing means by a carrier gas, and
   (e) analyzing said substances.

2. Method according to claim 1, further comprising subjecting said coated magnetic stirring element to ultrasound.

3. Method according to claim 1, wherein said coated magnetic stirring element is comprised of a magnetic support material surrounded by an inert casing selected from the group consisting of glass and plastic.

4. Method according to claim 1, wherein said coated magnetic stirring element is comprised of a magnetic support material coated with an active phase selected from the group consisting of polyethylene glycol, silicone, polyimide, octadecyltrichlorosilane, polymethylvinylchlorosilane, liquid-crystal poly-acrylates, grafted self-organized monomolecular layers and inorganic coating materials.

5. Method according to claim 1, further comprising removing said magnetic stirring element from said receptacle through a septum enclosing said receptacle, by means of an automatic discharging device, to a desorption tube.

6. Method according to claim 1, wherein said coated magnetic stirring element is a stirring ball.

7. Method according to claim 1, wherein said coated magnetic stirring element is a stirring rod.

8. Method according to claim 7, wherein said coated magnetic stirring element is a sheathed section of wire.

9. Method according to claim 1, wherein said solid-phase microextraction is performed thermally.

10. Method according to claim 9, wherein said solid-phase microextraction is performed dynamically.

11. Method according to claim 9, wherein said solid-phase microextraction is performed statically.

12. Method according to claim 1, wherein said solid-phase microextraction is performed using an organic liquid with a high level of interaction with said substances to be examined, and wherein (d) comprises transporting said desorbed substances by way of a syringe to a feeding device through which a carrier-gas stream flows.

13. Method according to claim 1, wherein (e) comprises analyzing said substances by gas chromatography.

14. Method for solid-phase microextraction and analysis of substances in a carrier fluid, comprising the steps of:
   (a) charging a receptacle containing an ultrasound stirrer with said carrier fluid and a coated collector element selected from the group consisting of a stirring rod, a stirring ball, and a sheathed metal wire,
   (b) subjecting said receptacle and its contents to ultrasound for a sufficient period of time to cause said substances to move intimately relative to said coated collector element,
   (c) performing solid-phase microextraction on said coated collector element to desorb said substances therefrom,
   (d) transporting said desorbed substances to analyzing means by a carrier gas, and
   (e) analyzing said substances.

15. Method according to claim 14, wherein said coated collector element is comprised of a magnetic support material surrounded by an inert casing selected from the group consisting of glass and plastic.

16. Method according to claim 14, wherein said coated collector element is comprised of a magnetic support material coated with an active phase selected from the group consisting of polyethylene glycol, silicone, polyimide, octadecyltrichlorosilane, polymethylvinylchlorosilane, liquid-crystal poly-acrylates, grafted self-organized monomolecular layers and inorganic coating materials.

17. Method according to claim 14, wherein said receptacle is closed by a septum, said method further comprising withdrawing, by means of an automatic discharging device, said coated collector element from said receptacle through said septum, and placing said withdrawn coated collector element in a desorption tube.

18. Method according to claim 14, wherein said coated collector element element is a stirring ball.

19. Method according to claim 14, wherein said coated collector element is a stirring rod.

20. Method according to claim 19, wherein said coated collector element is a sheathed section of wire.

21. Method according to claim 14, wherein said solid-phase microextraction is performed thermally.

22. Method according to claim 21, wherein said solid-phase microextraction is performed dynamically.

23. Method according to claim 21, wherein said solid-phase microextraction is performed statically.

24. Method according to claim 14, wherein said solid-phase microextraction is performed using an organic liquid with a high level of interaction with regard to the substances to be examined, and wherein (d) comprises transporting said desorbed substances by way of a syringe to a feeding device through which a carrier-gas stream flows.

25. Method according to claim 14, wherein (e) comprises analyzing said substances by gas chromatography.

26. Method for the solid-phase microextraction and analysis of substances in an environment, comprising the steps of:
   (a) exposing to said environment a collector element comprising a carrier made from magnetic material and which is suitable as a stirring element for a magnetic stirrer, said carrier coated with a member selected from the group consisting of a sorbent, an adsorbent and a combined sorbent and adsorbent, for a sufficient period of time for said collector element to sorb said substances from said environment,
   (b) performing solid-phase microextraction on said collector element to desorb said substances therefrom,
   (c) transporting said desorbed substances to analyzing means by a carrier gas, and
   (d) analyzing said substances.

27. Method for solid-phase microextraction and analysis of substances which are to be investigated in a gas phase above a carrier liquid, which contains the substances to be investigated, said method comprising contacting said gas phase with a collector for sufficient time to cause said substances to adhere to said collector from said gas phase, then subjecting said collector to solid-phase microextraction with respect to at least one substance adhering to said collector, and transporting substances thus desorbed for analysis by means of a carrier gas, wherein said collector is a hydrophobic hose having sorptive activity supported on an inert support, slid hydrophobic hose having a wall thickness of 0.2 to 1.5 mm.

28. Method according to claim 27 in which the wall thickness of said hydrophobic hose is from 0.5 to 1 mm.

29. Method according to claim 26, wherein the steps of sorption, of transport, of solid-phase microextraction and of analysis are carried out automatically.

30. Method according to claim 26, wherein said collector is removably attached to a holder.

31. Method according to claim 26, wherein said carrier liquid is heated and is additionally stirred.

32. Method according to claim 26, wherein said carrier liquid is arranged in a headspace vessel.

33. Method according to claim 27, wherein said inert support is a glass support or a magnetic rod-like support with a minimum internal diameter of 0.8 mm.

34. Method according to claim 27, wherein said inert support is a glass support or a magnetic rod-like support with an internal diameter of from 1.0 mm to 1.3 mm.

35. Method according to claim 27, wherein said hose is from 5 to 60 mm in length.

36. Method according to claim 27, wherein said collector used is formed integrally with a headspace vessel cap.

37. Method according to claim 27, wherein said hose is formed of a member selected from the group consisting of polydimethylsiloxane, polyethylene glycol, silicone, polyimide, octadecyltrichlorosilane, polymethylvinylchlorosilane, liquid-crystal polyacrylates, grafted self-organized monomolecular layers and inorganic coating materials.

38. Collector for the solid-phase microextraction and analysis of substances which are in a gas phase or in a carrier liquid, to be fitted into a solid-phase extraction apparatus, said collector comprising an inert, rod-like support with a hydrophobic hose which has a sorptive action on substances, has been pushed on and has a wall thickness of from 0.2 to 1.5 mm.

39. Collector according to claim 38, wherein said wall thickness is in the range of 0.5 to 1 mm.

40. Collector according to claim 38, wherein said support has an internal diameter of at least 0.8 mm.

41. Collector according to claim 38, wherein said support has an internal diameter of 1.0 to 1.3 mm.

42. Collector according to claim 38, wherein said is from 5 to 60 mm in length.

43. Collector according to claim 38, wherein said inert support is a glass support or a magnetic support.

44. Collector according to claim 38, wherein said collector is formed integrally with a headspace vessel cap.

45. Collector according to claim 38, further comprising a holder for detachably holding the collector.

46. Collector according to claim 38, wherein said is formed of a member selected from the group consisting of polydimethylsiloxane, polyethylene glycol, silicone, polyimide, octadecyltrichlorosilane, polymethylvinyi-chlorosilane, liquid-crystal polyacrylates, grafted self-organized monomolecular layers and inorganic coating materials.

* * * * *

UNITED STATES PATENT AND TRADEMARK OFFICE
CERTIFICATE OF CORRECTION

PATENT NO.    : 6,815,216 B2
DATED         : November 9, 2004
INVENTOR(S)   : Patrick Sandra et al.

It is certified that error appears in the above-identified patent and that said Letters Patent is hereby corrected as shown below:

Column 12,
Lines 3 and 9, kindly change "wherein said is" with -- wherein said support is --

Signed and Sealed this

Twenty-second Day of February, 2005

JON W. DUDAS
*Director of the United States Patent and Trademark Office*